United States Patent

Kooda et al.

Patent Number: 4,650,813
Date of Patent: Mar. 17, 1987

[54] ANTI-ALLERGIC HYDROXYBIPHENYL COMPOUNDS

[75] Inventors: Akihide Kooda, Gifu; Itsuo Nishioka, Fukuoka; Takeshi Nishiyori, Gifu; Shoji Yahara, Fukuoka, all of Japan

[73] Assignee: Kabushiki Kaisha Tsmurajuntendo, Tokyo, Japan

[21] Appl. No.: 708,566

[22] Filed: Mar. 6, 1985

Related U.S. Application Data

[62] Division of Ser. No. 534,702, Sep. 22, 1983, Pat. No. 4,537,996.

[30] Foreign Application Priority Data

Nov. 24, 1982 [JP] Japan ................. 57-204482

[51] Int. Cl.⁴ ............ A61K 31/05; A61K 31/11
[52] U.S. Cl. .................. 514/701; 514/719; 514/720; 514/733
[58] Field of Search ........... 514/699, 736, 701, 733, 514/719, 720

[56] References Cited

PUBLICATIONS

Sugii, Chemical Abstracts; 24:3505, (1930).

*Primary Examiner*—Leonard Schenkman
*Attorney, Agent, or Firm*—Birch, Stewart, Kolasch and Birch

[57] ABSTRACT

New hydroxybiphenyl compounds of the general formula:

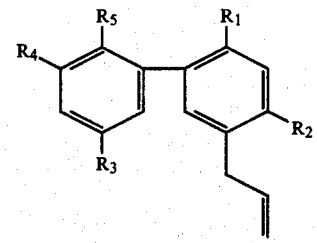

wherein $R_1$ stands for a hydrogen atom or a hydroxyl group, $R_2$ for a hydrogen atom or a hydroxyl group, $R_3$ for a hydroxyl group, a group of the formula $-CH_2-CH=CH_2$ or a group of the formula $-CH=CH-CHO$, $R_4$ for a hydrogen atom or a group of the formula

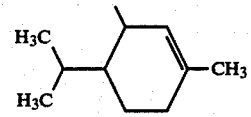

and $R_5$ for a hydroxyl group or a group of the formula

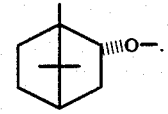

These compounds are obtained by extraction of "Tōkoboku", i.e. dried cortex of *Magnolia officinalis* which belongs to the family Magnoliaceae. They are useful as pharmaceuticals or intermediates therefor, in particular as anti-allergics.

12 Claims, No Drawings

ANTI-ALLERGIC HYDROXYBIPHENYL COMPOUNDS

This application is a divisional of copending application Ser. No. 534,702, filed on Sept. 22, 1983, now U.S. Pat. No. 4,537,996.

BACKGROUND OF THE INVENTION

1. Field of the Invention

This invention relates to new hydroxybiphenyl compounds. More particularly this invention relates to new hydroxybiphenyl compounds possessing anti-allergic activity, which can be obtained by extraction of "Tōkoboku" as will be specified below in more detail.

2. Description of the Prior Arts

"Tōkoboku" is a dried cortex preparation of "Karaho" (*Magnolia officinalis*) which belongs to the family Magnoliaceae. It is a drug of importance in Chinese medicine. Thus it has been used from of old in varied formulations of Chinese medicine in order to impart thereto such activity as analgesic and spasmolytic activity. An aqueous extract from "Tōkoboku" has been found to have a curare-like action and an ethereal extract therefrom has central nervous system-inhibitory, analgesic and spasmolytic actions. It is also reported that Magnolol, Honokiol and Magnocurarine, all contained in "Tōkoboku", have a musclerelaxant action mediated by the central nervous system. Most recently it was reported that an extract from "Tōkoboku" has an anti-allergic action, i.e. an pharmacological action which had not been reported in the literature [Nihon Yakurigakkaishi, 80, 31 (1982)].

SUMMARY OF THE INVENTION

We have extensively carried out extractions of "Tōkoboku" followed by separation of the extracts in exploration of the components responsible for the allergic activity. As a result of this, we have now succeeded in obtaining new hydroxybiphenyl compounds, on which the present invention is based.

Thus, according to the present invention, there are provided new hydroxybiphenyl compounds of the general formula (I)

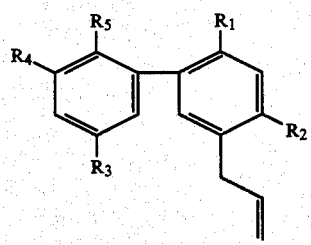

wherein $R_1$ stands for a hydrogen atom or a hydroxyl group, $R_2$ for a hydrogen atom or a hydroxyl group, $R_3$ for a hydroxyl group, a group of the formula —CH$_2$—CH=CH$_2$ or a group of the formula —CH=CH—CHO, $R_4$ for a hydrogen atom or a group of the formula

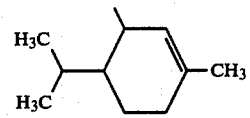

and $R_5$ for a hydroxyl group or a group of the formula

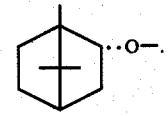

The new hydroxybiphenyl compounds of the general formula (I) are obtainable by subjecting "Tōkoboku" as the raw material to extraction and subsequent separation.

DETAILED DESCRIPTION OF THE INVENTION

The new hydroxybiphenyl compounds of the general formula (I) can be obtained, for example, in the following manner.

The "Tōkoboku" is extracted with water or methanol at room temperature and the extract is then concentrated. The thus concentrated extract is partitioned between water and ethyl acetate and the ethyl acetate layer is concentrated and the concentrate is then subjected to column chromatography on silica gel. Elution is carried out using solvents such as hexane, benzene, acetone and ethyl acetate, or mixtures of such solvents in varied ratios. The appropriate eluates are further subjected to column chromatography on silica gel, alumina and/or Sephadex LH-20, and the column is developed and eluted with solvents such as methanol, hexane:benzene, hexane:acetone, benzene:acetone, benzene:ethyl acetate, chloroform:acetone and chloroform:methanol.

The compounds of the invention are useful as pharmaceuticals or intermediates therefor, in particular as anti-allergic agents.

The following examples illustrate the preparation and physical properties of some of the compounds of the present invention.

The structures of the compounds shown in the examples were identified, in any case, on the basis of mass spectra, elementary analysis, IR spectra, UV spectra and NMR (PMR) spectra.

EXAMPLE 1

Four kg of "Tōkoboku" is ground and the ground product subjected twice to extraction with 9 l of water at room temperature for 24 hours. The extracts are combined and concentrated until 600 g of an extract is obtained. This extract is dissolved in 2 l of water and partitioned three times between ethyl acetate and the water. The ethyl acetate layer is concentrated until 300 g of the concentrate (i.e. extract) is obtained.

The concentrate is subjected to column chromatography on 500 g of silica gel, using as eluent solvent mixtures of benzene:ethyl acetate in increasing ratios of from 1:0 to 3:1. The eluates are collected as benzene, benzene:ethyl acetate (50:1), benzene:ethyl acetate (20:1), and benzene:ethyl acetate (3:1) eluates, each being a 100 ml fraction.

The solvent is distilled off from the benzene eluate fraction and the residue subjected to column chromatography on 50 g of alumina. The column is eluted with hexane:benzene (3:1) to give 400 mg of the compound of the following formula (II) as a colorless oil.

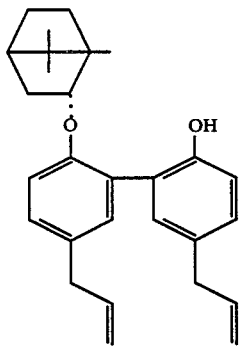

(II)

This compound was named Bornylmagnolol.
Mass spectrum: m/e 402 (M+).
Elementary analysis (for $C_{28}H_{34}O_2$): Calculated (%): C, 83.53; H, 8.51; O, 7.96. Found (%): C, 83.62; H, 8.31; O, 8.07.
Color, Physical form: Colorless oil.
Specific rotation: $[\alpha]_D^{20}$ −7.6° (C=1.67, CHCl$_3$).
UV spectrum ($\lambda_{max}^{MeOH}$ nm): 290 ($\epsilon$=8000).
NMR (PMR) spectrum ($\delta$ in CDCl$_3$): 0.80 (3H, s), 0.83 (3H, s), 0.87 (3H, s), 0.80–2.45 (7H, m), 3.36 (4H, m), 4.38 (1H, dd, J=2.5 Hz, 9 Hz), 4.90–5.20 (4H, m), 5.75–6.23 (2H, m), 6.28(OH, br.s), 6.80–7.25 (6H, m).

EXAMPLE 2

The solvents are distilled off from the benzene:ethyl acetate (50:1) eluate fraction obtained in Example 1. The residue is subjected first to column chromatography on 50 g of alumina using methanol as eluent, and then to column chromatography on 100 g of silica gel using as eluent hexane:acetone (10:1) to give 200 mg of the compound of the following formula (III) as a colorless oil.

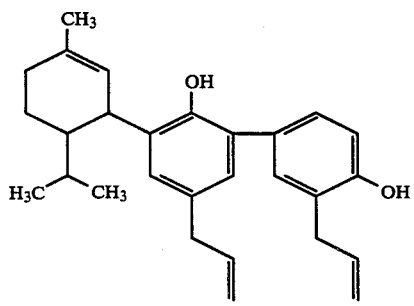

(III)

This compound was named Piperitylhonokiol.
Mass spectrum: m/e 402 (M+).
Elementary Analysis (for $C_{28}H_{34}O_2$): Calculated (%): C, 83.53; H, 8.51; O, 7.96. Found (%): C, 83.75; H, 8.14; O, 8.11.
Color, Physical form: Colorless oil.
Specific rotation: $[\alpha]_D^{20}$ −97.0° (C=0.69, CHCl$_3$).
UV spectrum ($\lambda_{max}^{MeOH}$ nm): 290 ($\epsilon$=7800).
NMR (PMR) spectrum ($\delta$ in CDCl$_3$): 0.83 (3H, d, J=6 Hz), 0.89 (3H, d, J=6 Hz), 1.72 (3H, br.s), 1.20–2.20 (6H, m), 3.30 (2H, d, J=6.5 Hz), 3.42 (2H, d, J=6.5 Hz), 3.50 (1H, m), 4.92–5.30 (4H, m), 5.41 (1H, br.s), 5.78–6.25 (2H, m), 6.80–6.90 (3H, m), 7.18–7.37 (2H, m).

EXAMPLE 3

The solvents are distilled off from the benzene:ethyl acetate (20:1) eluate fraction obtained in Example 1. The residue is subjected first to column chromatography on 50 g of Sephadex LH-20 using benzene:acetone (20:1) as eluent and then to column chromatography on 100 g of silica gel using chloroform: acetone (50:1) as eluent.

The eluent is distilled off from a fraction of the chloroform acetone (50:1) eluate, which fraction was confirmed by thin layer chromatography to contain a single constituent. The residue is crystallized from benzene to give 400 mg of the compound of the following formula (IV):

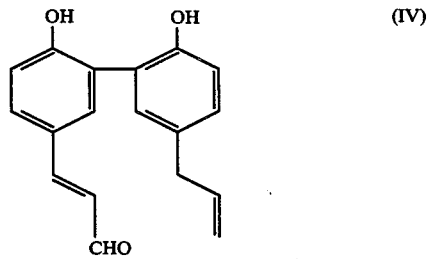

(IV)

as light yellow needles, m.p. 135°–136° C., as well as 400 mg of the compound of the following formula (V):

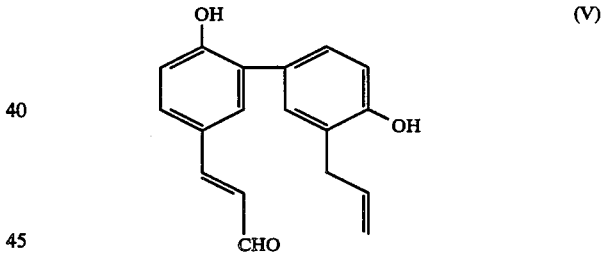

(V)

as light yellow needles, m.p. 153°–157° C.

The compounds of the formulas (IV) and (V) were named Magnaldehyde A and Magnaldehyde B, respectively:
Magnaldehyde A:
Mass spectrum: m/e 280 (M+).
Elementary analysis (for $C_{18}H_{16}O_3$): Calculated (%): C, 77.12; H, 5.75; O, 17.13. Found (%): C, 77.14; H, 5.81; O, 17.05.
Color, Physical form: Pale yellow needles.
Specific rotation: $[\alpha]_D^{20}$ ±0° (C=1.20, CHCl$_3$).
UV spectrum ($\lambda_{max}^{MeOH}$ nm): 373 ($\epsilon$=26,000), 330 ($\epsilon$=28,000).
IR spectrum ($\nu_{max}^{CHCl_3}$ cm$^{-1}$): 1675, 1625, 1605, 1580.
NMR spectrum ($\delta$ in acetone −d$_6$): 3.35 (2H, d, J=6.5 Hz), 4.90–5.20 (2H, m), 5.80–6.20 (1H, m), 6.65 (1H, dd, J=[Hz, 16 Hz), 6.90–7.65 (6H, m), 7.62 (1H, d, J=16 Hz), 9.61 (1H, d, J=8 Hz).
Magnaldehyde B:
Mass spectrum: m/e 280 (M+).

Elementary analysis (for $C_{18}H_{16}O_3$): Calculated (%): C, 77.12; H, 5.75; O, 17.13. Found (%): C, 77.15; H, 5.79; O, 17.06.

Color, Physical form: Pale yellow needles.
Melting point: 153°–157° C.
Specific rotation: $[\alpha]_D^{20}$ ±0° (C=1.00, $CHCl_3$).
UV spectrum ($\lambda_{max}^{MeOH}$ nm): 324 ($\epsilon$=33,000), 284 ($\epsilon$=40,000).
IR spectrum ($\nu_{max}^{CHCl_3}$ cm$^{-1}$): 1675, 1625, 1605, 1580.
NMR spectrum ($\delta$ in acetone-$d_6$): 3.44 (2H, m), 4.90–5.23 (2H, m), 4.85–5.24 (1H, m), 6.67 (1H, dd, J=8 Hz, 16 Hz), 6.92 (1H, d, J32 8 Hz), 7.03 (1H, d, J=8 Hz), 7.33 (1H, dd, J=2.5 Hz, 8 Hz), 7.37 (1H, br.s), 7.51 (1H, dd, J=2.5 Hz, 8 Hz), 7.60 (1H, d, J=2.5 Hz), 7.60 (1H, d, J=16 Hz), 9.62 (1H, d, J=8 Hz).

EXAMPLE 4

The eluent is distilled off from the benzene:ethyl acetate (3:1) eluate fraction obtained in Example 1. The residue is subjected first to column chromatography on 100 g of silica gel using benzene:ethyl acetate (20:1) as eluent and then to column chromatography on 100 g of silica gel using as eluent chloroform:methanol (150:1) and chloroform:methanol (20:1). The eluent is distilled off from the eluate fraction which was found to contain a single ingredient by thin layer chromatography. There are thus obtained 200 mg of the compound of the following formula (VI):

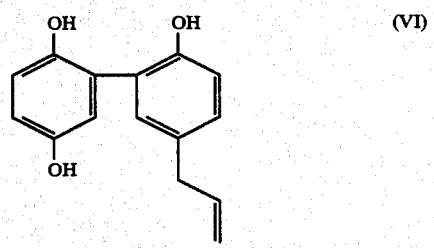

as a colorless oil as well as 300 mg of a yellow solid product.

The yellow solid product is recrystallized from benzene:chloroform to give 200 mg of the compound of the formula (VII):

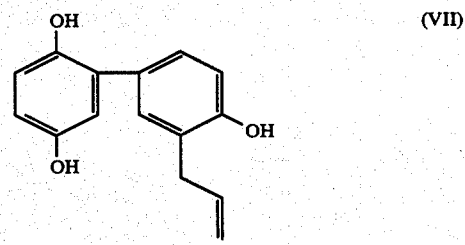

as pale yellow needles, m.p. 99°–100° C.

The compounds of the formulas (VI) and (VII) were named Magnotriol 1A and Magnotriol B, respectively.

Magnotriol A:
Mass spectrum: m/e 242 (M+).
Elementary analysis (for $C_{15}H_{14}O_3$):
Calculated (%): C, 74.37; H, 5.82; O, 19.81. Found (%): C, 74.45; H, 5.78; C, 19.77.
Color, Physical form: Colorless oil.
Specific rotation: $[\alpha]_D^{20}$ ±0° (C=1.10, $CHCl_3$).
UV spectrum ($\lambda_{max}^{MeOH}$ nm): 298 ($\epsilon$=5700).
NMR spectrum ($\delta$ in acetone-$d_6$): 3.35 (2H, m), 4.90–5.20 (2H, m), 5.29–3.20 (1H, m), 6.75 (1H, dd, J=3 Hz, 9 Hz), 6.79 (1H, d, J=3 Hz), 6.84 (1H, d, J=9 Hz), 6.94 (1H, d, J=9 Hz), 7.05 (1H, dd, J=2.5 Hz, 9 Hz), 7.11 (1H, br.s).

Magnotriol B:
Mass spectrum: m/e 242 (M+).
Elementary analysis (for $C_{15}H_{14}O_3$): Calculated (%): C, 74.37; H, 5.82; O, 19.81. Found (%): C, 74.47; H, 5.81; O, 19.72.
Color, Physical form: Pale yellow needles.
Melting point: 99°–100° C.
UV spectrum ($\lambda_{max}^{MeOH}$ nm): 306 ($\epsilon$=5100).
NMR spectrum ($\delta$ in acetone-$d_6$): 3.40 (2H, m), 4.90–5.20 (2H, m), 5.83–6.28 (1H, m), 6.65 (1H, dd, J=3 Hz, 9 Hz), 6.80 (1H, d, J=3 Hz), 6.84 (1H, d, J=9 Hz), 6.96 (1H, d, J=9 Hz), 7.28 (1H, dd, J=2.5 Hz, 9 Hz), 7.33 (1H, br.s).

These six new hydroxybiphenyl compounds are all obtained from the ethyl acetate extract, whose anti-allergic activity was determined by the following experimentation.

EXPERIMENTATION

Experiments were carried out in accordance with the Asherson and Ptak method for contact and delayed hypersensitivity in mice. Thus, male ddY mice, 8–10 weeks of age, were used and 0.1 ml of a 7% solution of picryl chloride in a carrier such as ethanol was applied to the abdomen of groups of ten animals each. Seven days after the sensitization, 0.02 ml of a 1% solution of picryl chloride in a carrier such as olive oil was applied to both ear lobes of each animal to induce contact dermatitis. Twenty four hours after the application, the thickness of the ear lobes was measured with a dial thickness guage (Ozaki Seisaku-sho). The values obtained by subtracting, from the thus measured thickness, the thickness of the ear lobes before the induction were used as a measure of swelling caused by the induced contact dermatitis.

The crude drug extracts to be tested, i.e. the aqueous extract, the ethyl acetate extract and EtOAc #2* extract, were each administered orally with a suitable carrier therefor at a dose of 50 mg/kg 16 hours after the induction of the contact dermatitis. The results are shown in the table.

TABLE

| Crude drug Extract to be tested | Dose (mg/kg) | Swelling (× $10^{-3}$ cm) | Inhibition (%) |
|---|---|---|---|
| Control | 50 | 5.22 ± 1.086 | |
| Aqueous extract | 50 | 3.69 ± 0.934 | 29.3 |
| Ethyl acetate extract | 50 | 3.49 ± 0.762 | 33.1 |
| EtOAc #2*extract | 50 | 2.49 ± 0.431 | 52.3 |

*Benzene:ethylacetate (3:1) eluate fraction

The results shown in the table show that the ethyl acetate extract has a greater inhibitory effect on contact dermatitis than the aqueous extract. Thus, they demonstrate that the six new hydroxybiphenyl compounds mentioned above possibly have an inhibitory effect on contact dermatitis.

What is claimed is:
1. A pharmaceutical composition containing as an active ingredient an effective anti-allergic amount of an hydroxybiphenyl compound of the formula:

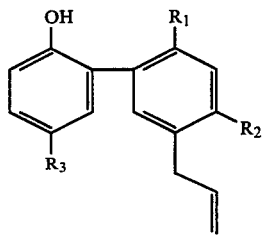

wherein one of $R_1$ and $R_2$ is a hydrogen atom and the other is a hydroxyl group and $R_3$ is a hydroxyl group or a group of the formula —CH=CH—CHO and a carrier therefor.

2. A pharmaceutical composition according to claim 1, wherein $R_1$ is a hydroxyl group, $R_2$ is a hydrogen atom and $R_3$ is a group of the formula —CH=CH—CHO.

3. A pharmaceutical composition according to claim 1, wherein $R_1$ is a hydrogen atom, $R_2$ is a hydroxyl group and $R_3$ is a group of the formula —CH=CH—CHO.

4. A pharmaceutical composition according to claim 1, wherein $R_1$ is a hydroxyl group, $R_2$ is a hydrogen atom and $R_3$ is a hydroxyl group.

5. A pharmaceutical composition according to claim 1, wherein $R_1$ is a hydrogen atom, $R_2$ is a hydroxyl group and $R_3$ is a hydroxyl group.

6. A method for treating delayed hypersensitivity reactions comprising administering to a host an effective anti-allergic amount of an hydroxybiphenyl compound of the formula:

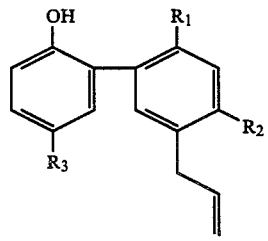

wherein one of $R_1$ and $R_2$ is a hydrogen atom and the other is a hydroxyl group and $R_3$ is a hydroxyl group or a group of the formula —CH=CH—CHO.

7. A method for treating delayed hypersensitivity reactions according to claim 6, wherein $R_1$ is a hydroxyl group, $R_2$ is a hydrogen atom and $R_3$ is a group of the formula —CH=CH—CHO.

8. A method for treating delayed hypersensitivity reactions according to claim 6, wherein $R_1$ is a hydrogen atom, $R_2$ is a hydroxyl group and $R_3$ is a group of the formula —CH=CH—CHO.

9. A method for treating delayed hypersensitivity reactions according to claim 6, wherein $R_1$ is a hydroxyl group, $R_2$ is a hydrogen atom and $R_3$ is a hydroxyl group.

10. A method for treating delayed hypersensitivity reactions according to claim 6, wherein $R_1$ is a hydrogen atom, $R_2$ is a hydroxyl group and $R_3$ is a hydroxyl group.

11. A pharmaceutical composition containing as an active ingredient an effective anti-allergic amount of an hydroxybiphenyl compound of the formula:

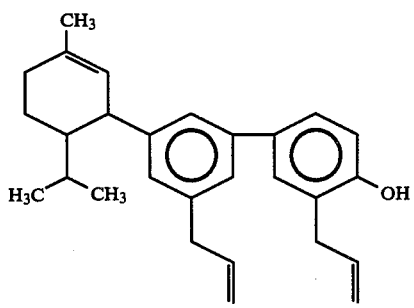

or of the formula:

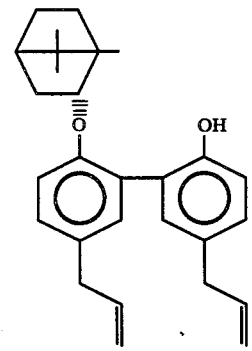

and a carrier therefor.

12. A method for treating delayed hypersensitivity reactions comprising administering to a host an effective anti-allergic amount of an hydroxybiphenyl compound of the formula:

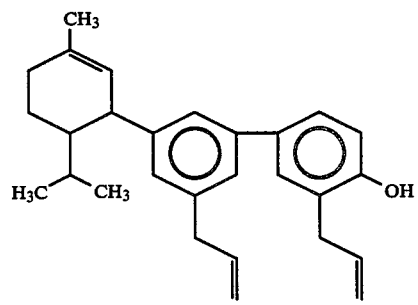

or of the formula:

* * * * *